US008776264B2

(12) United States Patent
Kiernan (10) Patent No.: US 8,776,264 B2
(45) Date of Patent: Jul. 15, 2014

(54) GARMENTS FOR PROVIDING ACCESS FOR SENSORS TO CONTACT SKIN

(75) Inventor: Pamela Kiernan, Darien, CT (US)

(73) Assignee: Ware LLC, Darien, CT (US)

(*) Notice: Subject to any disclaimer, the term of this patent is extended or adjusted under 35 U.S.C. 154(b) by 189 days.

(21) Appl. No.: 12/751,712

(22) Filed: Mar. 31, 2010

(65) Prior Publication Data

US 2010/0251454 A1      Oct. 7, 2010

Related U.S. Application Data

(60) Provisional application No. 61/166,415, filed on Apr. 3, 2009.

(51) Int. Cl.
*A41D 3/08* (2006.01)

(52) U.S. Cl.
USPC .................................................. 2/69

(58) Field of Classification Search
USPC ................... 2/114, 115, 69; 600/382
See application file for complete search history.

(56) References Cited

U.S. PATENT DOCUMENTS

| | | | | |
|---|---|---|---|---|
| 1,489,046 A | * | 4/1924 | Thompson | 2/114 |
| 3,409,007 A | * | 11/1968 | Fuller | 600/382 |
| 3,587,501 A | * | 6/1971 | Cruden, Jr. | 112/475.25 |
| 3,801,986 A | * | 4/1974 | Purdon | 2/69 |
| 4,055,855 A | * | 11/1977 | Ragone et al. | 2/105 |
| 4,239,046 A | * | 12/1980 | Ong | 600/391 |
| 4,446,575 A | * | 5/1984 | Davis | 2/400 |
| 4,488,314 A | * | 12/1984 | Johnson | 2/23 |
| 4,608,987 A | * | 9/1986 | Mills | 600/389 |
| 4,688,270 A | * | 8/1987 | Denicola et al. | 2/102 |
| 4,718,124 A | * | 1/1988 | Sawicki et al. | 2/114 |
| 4,729,377 A | * | 3/1988 | Granek et al. | 600/393 |
| 4,760,808 A | * | 8/1988 | Hulsmann | 112/68 |
| 4,824,103 A | | 4/1989 | Smidt | |
| 4,920,969 A | * | 5/1990 | Suzuki et al. | 600/436 |
| 4,930,161 A | * | 6/1990 | Cohen | 2/114 |
| D313,652 S | * | 1/1991 | Lavine | D24/168 |
| 5,007,427 A | * | 4/1991 | Suzuki et al. | 600/436 |
| 5,090,056 A | * | 2/1992 | Stoner et al. | 2/69 |

(Continued)

FOREIGN PATENT DOCUMENTS

GB    2465203 A    *    5/2010    ............... A41D 1/00

OTHER PUBLICATIONS

International Search Report for PCT/US2010/029630 dated Oct. 28, 2010.

(Continued)

*Primary Examiner* — Richale Quinn
(74) *Attorney, Agent, or Firm* — Edwards Wildman Palmer LLP; Joshua L. Jones; Alicia J. Esposito (57) ABSTRACT

A garment for wearing during monitoring of muscle activity of a subject includes a torso portion defining an interior space configured and adapted to accommodate and cover at least a portion of the subject's torso. The torso portion defines an exterior space external to the interior space. A plurality of access fittings are defined in the torso portion. Each access fitting is configured and adapted to accommodate access to skin of the subject adjacent a muscle group to be monitored by a sensor unit external to the torso portion, such that at least a portion of the sensor unit remains external to the torso portion with the sensor unit accessing the skin via the access fitting.

12 Claims, 4 Drawing Sheets

(56) References Cited

U.S. PATENT DOCUMENTS

| | | | |
|---|---|---|---|
| 5,184,351 A * | 2/1993 | Benstock | 2/114 |
| 5,368,042 A * | 11/1994 | O'Neal et al. | 600/546 |
| 5,505,208 A | 4/1996 | Toomim et al. | |
| 5,562,707 A * | 10/1996 | Prochazka et al. | 607/2 |
| 5,564,126 A * | 10/1996 | Chou | 2/114 |
| 5,643,329 A * | 7/1997 | Solomonow et al. | 607/43 |
| 5,689,829 A | 11/1997 | Rose | |
| 5,694,939 A | 12/1997 | Cowings | |
| 5,748,845 A | 5/1998 | Labun et al. | |
| 5,755,674 A | 5/1998 | Watson | |
| 5,802,611 A * | 9/1998 | McKenzie et al. | 2/69 |
| 5,822,802 A * | 10/1998 | Chou | 2/227 |
| 5,887,279 A * | 3/1999 | Elting et al. | 2/69 |
| D408,117 S * | 4/1999 | Wade | D2/728 |
| 5,913,407 A * | 6/1999 | Keyes | 2/83 |
| 6,006,129 A | 12/1999 | Watson | |
| 6,065,154 A * | 5/2000 | Hulings et al. | 2/102 |
| 6,102,899 A * | 8/2000 | Yimin | 604/385.01 |
| 6,148,444 A * | 11/2000 | Holmes et al. | 2/69 |
| 6,276,176 B1 | 8/2001 | Blakely | |
| 6,315,009 B1* | 11/2001 | Jayaraman et al. | 139/387 R |
| D457,290 S * | 5/2002 | Thompson | D2/743 |
| 6,438,758 B1* | 8/2002 | Burkard et al. | 2/115 |
| 6,453,204 B1* | 9/2002 | Rhodes | 607/149 |
| 6,458,060 B1 | 10/2002 | Watterson et al. | |
| 6,477,710 B1* | 11/2002 | Ojoyeyi | 2/69 |
| 6,571,115 B2* | 5/2003 | Axelgaard et al. | 600/388 |
| 6,647,552 B1* | 11/2003 | Hogan | 2/114 |
| 6,681,404 B1 | 1/2004 | Adlard et al. | |
| 6,755,795 B2 | 6/2004 | Marmaropoulos et al. | 600/587 |
| 6,792,622 B2* | 9/2004 | Graves | 2/114 |
| 6,850,791 B1* | 2/2005 | Axelgaard et al. | 600/388 |
| 6,913,559 B2 | 7/2005 | Smith | |
| D513,660 S * | 1/2006 | Greene | D2/742 |
| D513,828 S | 1/2006 | Bevier | |
| 6,991,586 B2 | 1/2006 | Lapcevic | |
| 7,072,721 B1* | 7/2006 | Trent | 607/149 |
| 7,150,710 B2 | 12/2006 | Haber et al. | |
| 7,166,064 B2 | 1/2007 | Watterson et al. | |
| 7,211,053 B2* | 5/2007 | Marmaropou | 600/587 |
| 7,245,956 B2* | 7/2007 | Matthews et al. | 600/382 |
| 7,324,841 B2 | 1/2008 | Reho et al. | |
| 7,418,741 B2* | 9/2008 | Rogers | 2/114 |
| 7,526,816 B2* | 5/2009 | Shak | 2/114 |
| 7,558,622 B2 | 7/2009 | Tran | |
| 7,628,675 B2* | 12/2009 | Staub | 450/28 |
| 7,645,213 B2 | 1/2010 | Watterson et al. | |
| 7,673,348 B2* | 3/2010 | Williams | 2/115 |
| 7,762,953 B2* | 7/2010 | Derchak et al. | 600/300 |
| 7,797,039 B2* | 9/2010 | Koivumaa et al. | 600/521 |
| 7,810,171 B2* | 10/2010 | Moore | 2/104 |
| D635,331 S * | 4/2011 | Eckman et al. | D2/742 |
| 7,942,856 B2* | 5/2011 | Lentini | 604/345 |
| 8,069,497 B2* | 12/2011 | Sheward et al. | 2/114 |
| 2002/0138125 A1* | 9/2002 | Axelgaard et al. | 607/149 |
| 2004/0009731 A1 | 1/2004 | Rabinowicz | |
| 2005/0049517 A1 | 3/2005 | Mathew et al. | |
| 2005/0178201 A1 | 8/2005 | Impio et al. | |
| 2006/0211937 A1 | 9/2006 | Eldridge | |
| 2006/0276704 A1 | 12/2006 | McGinnis et al. | |
| 2007/0083096 A1 | 4/2007 | Paradiso | |
| 2010/0041974 A1 | 2/2010 | Ting et al. | |
| 2011/0004088 A1* | 1/2011 | Grossman | 600/382 |
| 2011/0060252 A1* | 3/2011 | Simonsen et al. | 600/595 |

OTHER PUBLICATIONS

Written Opinion of the International Searching Authority for PCT/US2010/029630 dated Oct. 28, 2010.

* cited by examiner

GARMENTS FOR PROVIDING ACCESS FOR SENSORS TO CONTACT SKIN

CROSS-REFERENCE TO RELATED APPLICATIONS

This application claims benefit of priority to U.S. Provisional Patent Application No. 61/166,415, filed Apr. 3, 2009, which is incorporated by reference herein in its entirety.

BACKGROUND OF THE INVENTION

1. Field of the Invention

The present invention relates to electrical sensors used in treatment and monitoring of human and animal bodies, and more particularly to wearable garments that provide direct and easy access for such sensors to contact skin.

2. Description of Related Art

Sensing and treatment devices that require contact with the surface of the skin are well-known in the art. It is also well-known that such devices require close and direct access to the skin of the subject being treated or tested.

One exemplary sensor requiring access to the skin is an sEMG (surface electromyography) sensor used for sensing muscle activity. sEMG technology is a state of the art way of determining real-time information about the functioning of body parts, especially muscles. Muscle tissue contracts and relaxes as a function of the presence or absence of biologically generated electrical signals. sEMG sensors can be employed to detect such electrical signals. sEMG technology can be found in such fields as athletic training, physical rehabilitation medicine, biofeedback during strength training, and the like. sEMG monitoring equipment can be mounted in a medical cart or the like for use in a medical setting, with wires connecting the processing equipment, such as a computer system and display, in the cart with the sensors on the patient. Various sensors have recently been incorporated in gym equipment, for example as in U.S. Pat. No. 7,645,213 to Watterson et al., and in rehabilitation equipment. Portable electromyogram devices are known for example from U.S. Patent Application Publication No. 2005/0049517. Such portable devices can be worn around an arm or leg to detect muscle engagement during a work out, for example.

sEMG and other similar sensors include one or more individual sensors attached to a power source, a signal processor, and optionally one or more displays. Preferably, an electromyogram sensor joins its housing in such a fashion as to permit the sensor to detect muscle activity when the housing is conformably disposed about a body part such as an arm or leg, as described in the above-cited publication. If this is not possible or convenient, for example if it is desired to monitor chest or shoulder muscles, remote wired or wireless sensors can be adhered to the skin directly above the muscle group to be monitored. The data can be sent via wires or wirelessly from the sensor to the signal processor.

The current state of the art requires garments worn by the subject to be removed, rolled up, or otherwise adjusted to accommodate sensors if the muscles or tissues of interest are covered by the garment. For example, use of an sEMG sensor can require untucking or unbuttoning of a shirt, rolling up a sleeve or pant leg, removal or pulling down of a sock, or the like, in order to gain access to monitor a desired muscle group. These arrangements can cause undue stress on sensors and leads, and in some cases dislodge the sEMG sensor from the skin entirely. These arrangements can also be painful or uncomfortable. Moreover, these arrangements can be undependable, if for example, the pant leg or shirt sleeve is not rolled up tightly enough, especially while in motion. Depending on the design of the garment being worn, and the desired sensing location, direct sensor contact with the skin can require complete removal of the garment, as is done, for example during electrocardiography testing. Discomfort and embarrassment can result for the person having to remove or adjust garments to accommodate proper sensor access, either in public or in private. In a gym or physical rehabilitation facility, for example, use of such sensors on certain muscles can be precluded because it is not permissible or desirable to disrobe to the necessary extent to allow proper sensor access to the muscle group.

Such conventional methods and systems have generally been considered satisfactory for their intended purpose. However, there is still a need in the art for a garment that allows for significantly improved access of electrical sensors to monitor muscles. There also remains a need in the art for such a garment that is easy to make and use. The present invention provides a solution for these problems.

SUMMARY OF THE INVENTION

The subject invention is directed to a new and useful garment for wearing during monitoring of muscle activity of a subject. The garment includes a torso portion defining an interior space configured and adapted to accommodate and cover at least a portion of the subject's torso. The torso portion defines an exterior space external to the interior space. At least one opening, e.g., a waist opening, is defined in the torso portion from the exterior space to the interior space for accommodating the garment being put on and taken off of the subject's torso. A plurality of access fittings are defined in the torso portion. Each access fitting is configured and adapted to accommodate access to skin of the subject adjacent a muscle group to be monitored by a sensor unit external to the torso portion, such that at least a portion of the sensor unit remains external to the torso portion with the sensor unit accessing the skin via the access fitting.

In certain embodiments, the torso portion is configured to be worn on a subject's lower torso, e.g., as pants, shorts, or the like. The garment can include two legs attached to the torso portion for accommodating the subject's legs. Each leg can include a plurality of access fittings. Each leg can include an access fitting adjacent a hamstring portion of the leg, configured to provide access to skin adjacent the subject's hamstrings. It is also contemplated that each leg can include an access fitting adjacent a quadriceps portion of the leg, generally opposite the hamstring portion, configured to provide access to skin adjacent to the subject's quadriceps. The torso portion can includes a plurality of access fittings proximate a gluteus maximus portion located superior to the access fittings in the hamstring portion, configured to provide sensor access to skin adjacent the subject's gluteus maximus. It is also contemplated that each leg can include at least one access fitting configured to provide sensor access to skin adjacent the subject's lower leg muscles. For example, each leg can include at least one shin access fitting configured to provide sensor access to skin adjacent the subject's shin muscles, and at least one calf access fitting generally opposite the at least one shin access fitting configured to provide sensor access to the subject's calf muscles.

In certain embodiments, the torso portion is configured to be worn on a subject's upper torso, e.g., as a shirt. The garment can include two sleeves attached to the torso portion for accommodating the subject's arms. Each sleeve can include a plurality of access fittings. Each sleeve can include at least one upper arm access fitting configured to provide sensor access to skin adjacent the subject's upper arm muscles. Each sleeve can include at least one lower arm access fitting inferior with respect to the upper arm access fitting thereof for providing sensor access to skin adjacent the subject's lower arm muscles. The torso portion can include at least one abdominal access fitting configured to provide sensor access to skin adjacent the subject's abdominal muscles. It is also contemplated that the torso portion can include at least one chest access fitting superior with respect to the at least one abdominal access fitting configured to provide sensor access to skin adjacent the subject's chest muscles. The torso portion can include at least one lumbar access fitting opposite at least one abdominal access fitting configured to provide access to skin adjacent the subject's lumbar muscles. It is also contemplated that the torso portion can include at least one shoulder access fitting superior with respect to the at least one lumbar access fitting for providing access to skin adjacent the subject's shoulder muscles. The torso portion can include at least one gluteus maximus access fitting inferior with respect to the at least one lumbar access fitting for providing access to skin adjacent the subject's gluteus maximus.

In certain embodiments, each access fitting includes a slit defined through the torso portion for passage of a portion of a sensor device therethrough. The slit can be covered by a pocket, flap, or the like, or can be exposed without any covering, and can include a closure device such as a zipper, hook-and-loop fastener, or the like. It is contemplated that the access fittings can have a width that is open at all times, and/or can be incorporated into a patch, decorative design, logo, or the like. It is also contemplated that some or all of the access fittings can include a patch of electrically conductive material configured to allow sensor access to the subject's skin by way of electrical signals conducted from the subject's skin, through the patch, to the sensor with the sensor located completely outside the interior space of the torso portion of the garment.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION OF THE PREFERRED EMBODIMENTS

Figure 1:
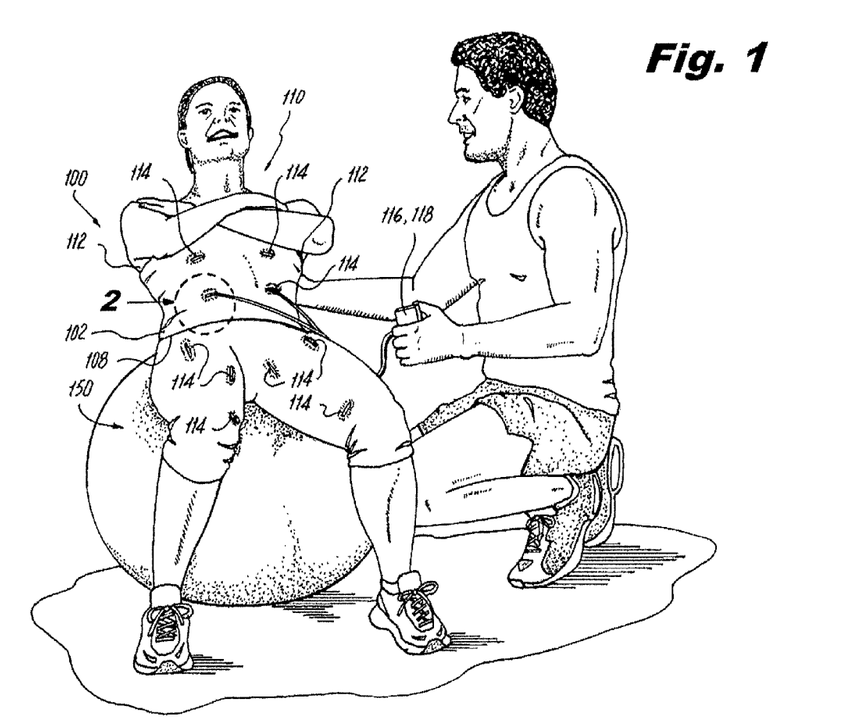
FIG. 1 is a perspective view of exemplary embodiments of garments constructed in accordance with the present invention, showing a subject wearing the garment during training with an sEMG or other monitoring device connected to the subject's abdomen through an access fitting in the garment to monitor muscle engagement during sit-ups.

Reference will now be made to the drawings wherein like reference numerals identify similar structural features or aspects of the subject invention. For purposes of explanation and illustration, and not limitation, a partial view of an exemplary embodiment of a garment in accordance with the invention is shown in FIG. 1 and is designated generally by reference character 100. Other embodiments of garments in accordance with the invention, or aspects thereof, are provided in FIGS. 2-9, as will be described. The systems and methods of the invention can be used to provide access for sensors to a subject's skin without requiring removal of the garment, rolling up of the garment, or the like.

Garment 100 is configured for wearing during monitoring of muscle activity of a subject, such as during working out, physical therapy, or any other suitable activity. Garment 100 includes a torso portion 102 defining an interior space 104 (not visible in FIG. 1, but see FIG. 2) configured and adapted to accommodate and cover at least a portion of the subject's torso, which in the case of garment 100 in FIG. 1 is the upper torso, as in a shirt or sweater, or other similar garment, and in the case of garment 150 in FIG. 1 is a lower garment. Torso portion 102 defines an exterior space 106 external the interior space 104, i.e., interior space 104 and exterior space 106 are the inside and outside of the garment, respectively, when it is being worn. A waist opening 108, a neck opening 110, and two sleeve openings 112 are defined in the torso portion 102 from the exterior space to the interior space for accommodating the garment being put on, worn, and taken off of the subject's torso. A plurality of access fittings 114 are defined in the torso portion 102. Each access fitting 114 is configured and adapted to allow immediate access to skin of the subject adjacent to a muscle group to be monitored by a sensor unit, e.g. sensor unit 116, external to the torso portion 102, such that at least a portion of the sensor unit remains external to the torso portion 102 with the sensor unit accessing the skin via the access fitting.

With continued reference to FIG. 1, access fittings 114 allow sensor unit 116, the main processor portion 118 of which remains outside of garment 100 during use, to have access for sensor lead 120 to pass through garment 100. In the exemplary use shown in FIG. 1, sensor unit 116 has leads 120 passing through access fittings 114 in torso portion 102 so that the subject wearing garment 100 and/or a personal trainer can monitor engagement of the subject's left and right external abdominal oblique muscles during sit-ups. The sensor unit 116 includes wires, but wireless sensors can also be used with garment 100.

Figure 2:
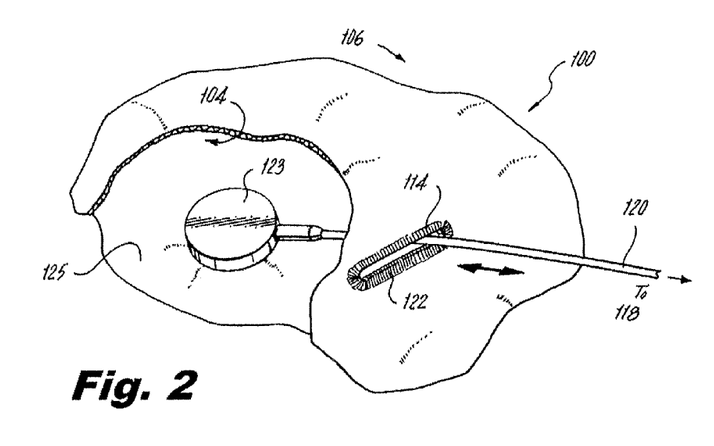
FIG. 2 is an enlarged perspective view of a portion of the garment of FIG. 1, showing an access fitting in the form of a slit providing access for a sensor lead through the garment for a device outside the garment to be able to sense the subject's muscle engagement.

Referring now to FIG. 2, a sensor lead 120 is shown passing through an access fitting 114 in garment 100. Access fitting 114 is a slit, reinforced with optional tubing 122, which can be stitching or embroidering, or other suitable reinforcement, passing from interior space 104 to exterior space 106. At the end of lead 120 is a sensor 123 that can be adhered to the skin 125 just superficial to a muscle group that is the desired target for monitoring. A portion of garment 100 in FIG. 2 is shown cut away to reveal sensor 123 and skin 125 inside garment 100. The length of the slit or opening of access fitting 114 can be of any suitable length or width for accommodating a particular type of sensor therethrough. Access fittings 114 allow for sensors, wired or wireless, to be used, removed, and replaced in different access fittings 114 without the subject wearing garment 100 having to disrobe entirely, roll up, or otherwise unduly adjust garment 100. Thus, the slit length should be long enough to accommodate sensors passing therethrough but not be so long as to be overly revealing. For example, slits for sEMG leads can be around 1 inch in length or up to 4 inches in length or more as needed for particular applications. Slits can be sized appropriately depending on the material used in the garment. For example, smaller slits can be used in garments made of stretchable material than in garments made of non-stretchable material, since a stretchable slit can stretch to accommodate sensors larger than itself. Those skilled in the art will readily appreciate that any suitable slit dimensions can be used without departing from the spirit and scope of the invention.

By way of comparison, using a traditional garment, as in the state of the art described above, to test muscle engagement in various muscle groups would require complete removal of the subject's shirt, or else wiring the lead through the neck, sleeves, or waist opening, since conventional active wear, gym attire, and the like, provides no other access openings, with the possible exception of a fly, which does not provide a practical access where modesty is concerned. With snug fitting work out garments, wiring through the neck, sleeves, or waist opening may not be possible or practical, and with loose garments, the weight or tension of the garment against the lead can damage the lead, sensor, and/or sensor unit or dislodge the sensor from the desired location on the skin.

Figures 3, 4:
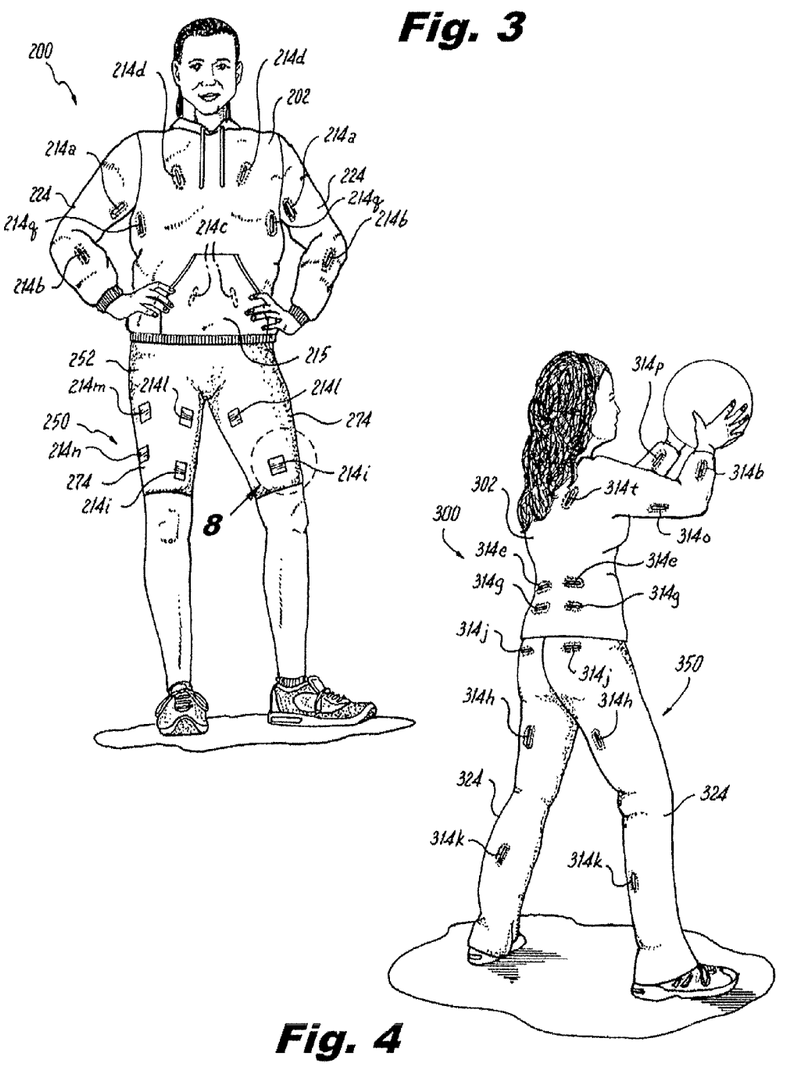
FIG. 3 is a front perspective view of exemplary embodiments of upper and lower garments constructed in accordance with the present invention, showing a subject wearing upper and lower garments and showing multiple exemplary locations for access fittings in each garment as viewed from the front.
FIG. 4 is a rear perspective view of exemplary embodiments of upper and lower garments constructed in accordance with the present invention, showing a subject wearing upper and lower garments and showing multiple exemplary locations for access fittings in each garment as viewed from the back.

Referring now to FIG. 3, another exemplary garment 200 is shown from the front. Garment 200 is a hooded sweatshirt that includes two sleeves 224 attached to torso portion 202 for accommodating the subject's arms. Each sleeve 224 includes an one upper arm access fitting 214a configured to provide sensor access to skin adjacent the subject's upper arm muscles, e.g. biceps and/or deltoids. Each sleeve includes at least one lower arm access fitting 214b inferior with respect to upper arm access fitting 214a thereof (when the arms are straight down) for providing sensor access to skin adjacent the subject's lower arm muscles. Torso portion 202 includes abdominal access fittings 214c configured to provide sensor access to skin adjacent the subject's abdominal muscles, and chest access fittings 214d superior with respect to abdominal access fittings 214c for providing sensor access to skin adjacent the subject's chest muscles. Access fittings 214q are provided in the ribs portion of the garment for accessing the subject's rib muscles, such as the serratus anterior muscles. An optional pocket or pouch 215 covers access fittings 214c, and the hood is also optional. Additionally, those skilled in the art will readily appreciate that garments in accordance with the invention can be tight, relatively loose, or any suitable combination of both without departing from the spirit and scope of the invention.

Reference is now made to FIG. 4, which shows an exemplary garment 300 from the back. Garment 300 is a long sleeve shirt that can have the same access fittings in the front as in garment 200. Torso portion 302 includes lumbar access fittings 314e that are generally opposite the abdominal access fittings (not shown but see 214c in FIG. 3) for providing access to skin adjacent the subject's lumbar muscles. Shoulder access fittings 314f are provided superior with respect to lumbar access fittings 314e for providing access to skin adjacent the subject's shoulder muscles. Triceps access fittings 314o are provided in a triceps portion of the sleeve for access to the subject's triceps muscles. Near the wrists openings of the sleeves, lower arm access fittings 314p and 314b are provided in the bottom and top portions, respectively, of the lower arms of the sleeves to provide access to the muscles on the top and bottom of the subject's lower arms. Gluteus maximus access fittings 314g are located inferior with respect to lumbar access fittings 314e, e.g., in the seat of garment 300, for providing access to skin adjacent the subject's gluteus maximus. While not shown in FIG. 3, similar access fittings can be included in the rear of garment 200 as well.

With continued reference to FIGS. 3-4, garment 250 includes a torso portion 252 configured to be worn on a subject's lower torso, e.g., as shorts. Garment 250 includes two legs 274 attached to torso portion 252 for accommodating the subject's legs. Each leg 274 includes an access fitting in a hamstring portion of the respective leg 274 (not shown but see 314h in FIG. 4), configured to provide access to skin adjacent the subject's hamstring muscles. Each leg 274 includes access fittings 214i adjacent a quadriceps portion of the respective leg 274, generally opposite the hamstring portion thereof, configured to provide access to skin adjacent to the subject's quadriceps muscles. Adductor access fittings 214l are included for monitoring adductor muscle engagement. Access fittings 214m and 214n are provided substantially lateral with respect to access fittings 214l and 214i, respectively, to provide access to lateral portions of the subject's upper and lower thighs. Access fittings are provided in a gluteus maximus portion of garment 200 (not shown, but see 314j in FIG. 4), located superior to the access fittings in the hamstring portion thereof, configured to provide sensor access to skin adjacent the subject's gluteus maximus and/or gluteus medius muscles.

Referring now to FIG. 4, pants garment 350 includes the access fittings 314h and 314j described above, and includes access fittings in the front at the locations shown in garment 250 of FIG. 3. Each leg 324 also includes a calf access fitting 314k configured to provide sensor access to skin adjacent the subject's calf muscles, and a shin access fitting (not shown) generally opposite the respective calf access fitting 314k configured to provide sensor access to the subject's shin muscles can optionally be included.

The garments above have been described in the exemplary context of shorts, pants, knickers, sweatshirts, and short sleeve shirts. Other exemplary garment configurations include sleeveless shirts, cropped shirts, trousers, vests, undergarments, coats, parkas, snow pants, construction overalls, and the like. Those skilled in the art will readily appreciate that any suitable garment type or configuration can be used, any other suitable access fitting locations can be used, and any of the access fittings shown herein can optionally be omitted in a garment without departing from the spirit and scope of the invention. Suitable materials for garments constructed in accordance with the present invention include spandex, terry cloth, cotton, and fleece. Those skilled in the art will readily appreciate that these materials are exemplary only, and that any suitable material can be used for a particular application without departing from the spirit and scope of the invention.

Figure 5:
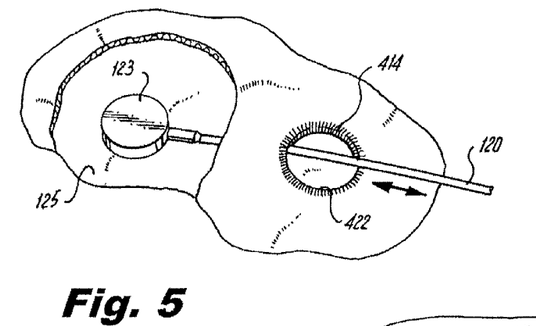
FIG. 5 is a perspective view of an exemplary embodiment of an access fitting in a garment constructed in accordance with the present invention, showing an access fitting with a round, open aperture through the garment.
Figures 6, 7:
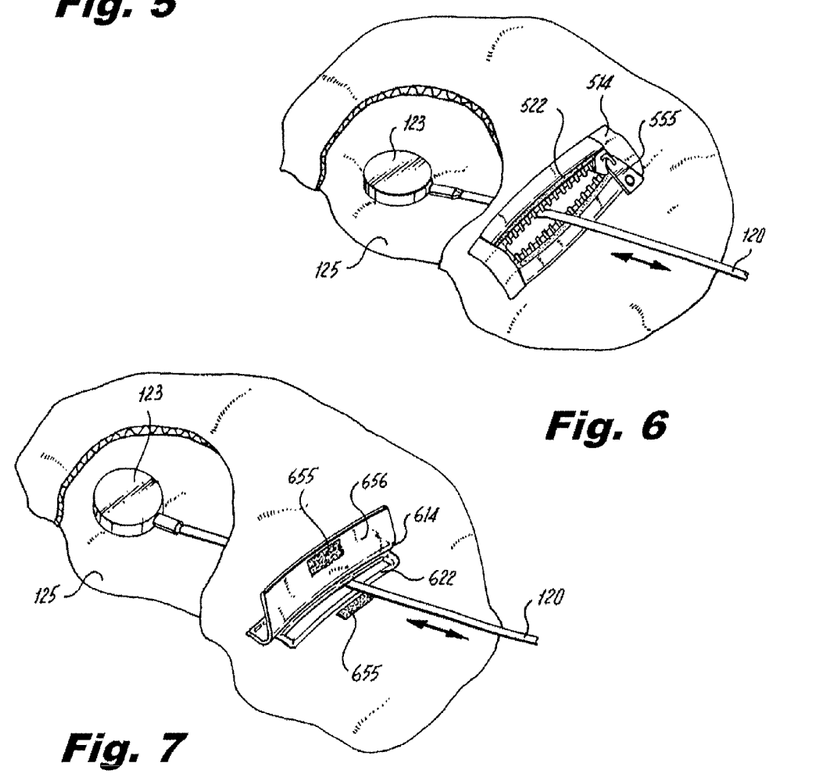
FIG. 6 is a perspective view of another exemplary embodiment of an access fitting in a garment constructed in accordance with the present invention, showing an access fitting having a slit through the garment incorporating a zipper for closing the slit.
FIG. 7 is a perspective view of another exemplary embodiment of an access fitting in a garment constructed in accordance with the present invention, showing an access fitting having a slit through the garment incorporating a flap with a hook-and-loop closure for concealing the slit.

With reference now to FIG. 5, another embodiment of access fitting 414 is shown, which includes a generally round opening 422 in lieu of a slit. FIG. 6 shows another embodiment of access fitting 514 in which the slit 522 includes a zipper 555 for closing slit 522 fully or partially. FIG. 7 shows another embodiment of an access fitting 614, in which slit 622 can be covered by flap 656. Flap 656 includes a hook-and-loop closure device 655 for securely concealing slit 622 when not in use. Buttons, clasps, or any other suitable closure device can be used without departing from the spirit and scope of the invention. Access fittings in accordance with the present invention can be incorporated in patches, embroidery, logos, decorative design features, or the like. Those skilled in the art will readily appreciate that the slits and openings described herein are exemplary and that any suitable opening type, fenestration, or the like can be used without departing from the spirit and scope of the invention.

Figure 8:
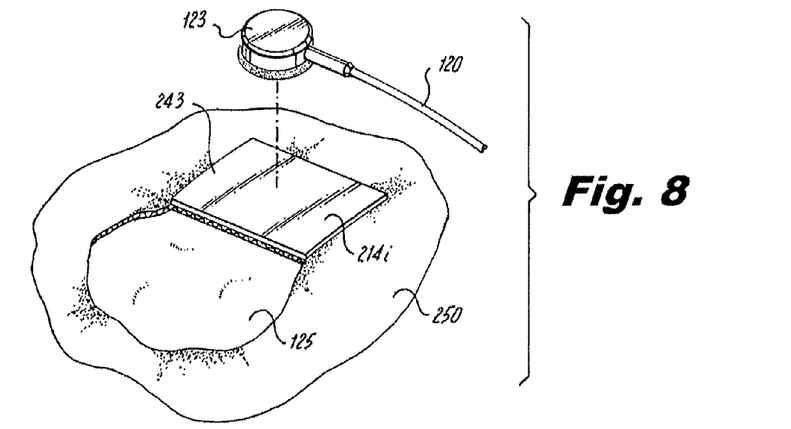
FIG. 8 is a perspective view of another exemplary embodiment of an access fitting in a garment constructed in accordance with the present invention, showing an access fitting having a conductive patch in the garment for providing sensor access to the underlying skin while keeping the sensor completely external to the garment.

FIG. 8 shows yet another embodiment of an access fitting 214*i* in which there is no opening or slit. Instead, a patch 243 of electrically conductive material is used to allow sensors to make electrical contact with the underlying skin 125. In this way, electrical signals can be conducted from the subject's skin, through patch 243, to a sensor located completely outside the interior space of the garment, e.g., attached to the outside surface of patch 243. Access fitting 214*i* is shown also in FIG. 3. In FIG. 8, a portion of garment 250 is cut away to reveal the underlying skin 125. For the best electrical contact, garments using this type of access fitting are preferably tight to the skin, at least locally around the access fittings. Suitable electrically conductive materials for garments are described, for example in U.S. Patent Application Publication No. 2004/0009731 to Rabinowicz, which is incorporated herein by reference in its entirety.

Figure 9:
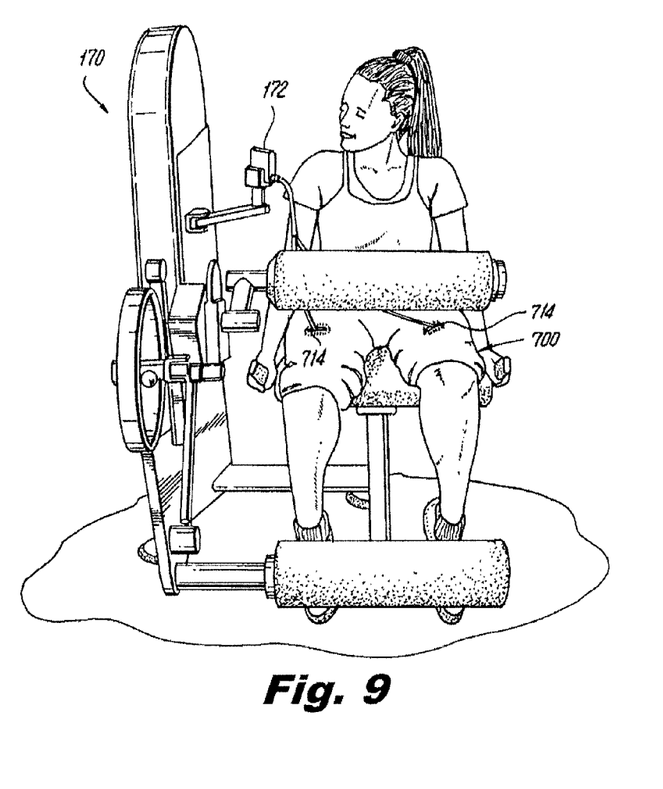
FIG. 9 is a perspective view of exemplary embodiments of garments constructed in accordance with the present invention, showing the garments being worn by a subject who is using gym equipment that has sensors incorporated therewith, accessing the subject's skin through access fittings in the garment to monitor muscle activity.

Referring now to FIG. 9, use of a garment such as those described above is contemplated for allowing access to the wearer's skin during use of gym equipment, physical therapy equipment, diagnostic equipment, and the like, that incorporates sensors like sEMG sensors. FIG. 9 shows a subject using a workout machine 170 wearing garment 700. Machine 170 has a built in sensor unit 172. The subject can monitor muscle engagement for training or safety purposes attaching sensors 123, connected to sensor unit 172 via leads 120, or wirelessly, as described above, to skin adjacent a key muscle group being exercised by machine 170, in this case the thigh muscles, but such a sensor can be applied to any other particular muscle group as well. Access fittings 714 in garment 700 allow leads 120 to pass through garment 700 without requiring disrobement, whether partial or total. Time is also saved by having convenient access for multiple muscle groups without having to rearrange or remove garments. As the subject moves from machine to machine throughout a workout, for example, different access fittings can provide convenient, immediate, personal, private, and successful access to the different muscles being exercised. The same also applies to moving from exercise to exercise where no machines are used, or from exercise to exercise in physical therapy or rehabilitation, or the like.

While described herein with the exemplary application of providing access for sEMG sensors, those skilled in the art will readily appreciate that this is an exemplary application only. Any suitable sensors can be used with garments constructed in accordance with the invention, whether wired or wireless. The garments described above can be used to allow wires to pass through the garment directly to be attached to a sensor already on the skin, or any electronic device underneath the garment, such as a music player or other mobile device. Garments as described herein can be used to provide quick access to apply treatment such as electrical pulses for defibrillation purposes, for example, which may be needed during physical therapy, rehabilitation, or the like.

The methods and systems of the present invention, as described above and shown in the drawings, provide access for muscle engagement sensors while allowing the user to remain fully clothed, without having to fully or partially disrobe or otherwise unduly adjust garments to accommodate proper sensor access. While the apparatus and methods of the subject invention have been shown and described with reference to preferred embodiments, those skilled in the art will readily appreciate that changes, different combinations, and/or modifications may be made thereto without departing from the spirit and scope of the subject invention.

What is claimed is:

1. A shirt for wearing during monitoring of muscle activity of a subject comprising:
   a) a torso portion defining an interior space configured and adapted to accommodate and cover at least a portion of the subject's upper torso, and defining an exterior space external to the interior space, wherein at least one opening is defined in the torso portion from the exterior space to the interior space for accommodating the garment being put on and taken off of the subject's upper torso;
   b) a pair of sleeves attached to the torso portion and defining arm portions of the interior space for accommodating the subject's arms; and
   c) a plurality of access fittings defined in at least one of the torso portion and the pair of sleeves, each access fitting being configured and adapted to accommodate access to skin of the subject adjacent a muscle group to be monitored by a sensor unit external to the torso portion, such that at least a portion of the sensor unit remains external to the torso portion with the sensor unit accessing the skin via the access fitting, wherein the plurality of access fittings includes at least one abdominal access fitting configured to provide sensor access to skin adjacent the subject's abdominal muscles, at least one chest access fitting superior with respect to the at least one abdominal access fitting configured to provide sensor access to skin adjacent the subject's chest muscles, at least one lumbar access fitting opposite the at least one abdominal access fitting configured to provide access to skin adjacent the subject's lumbar muscles, at least one shoulder access fitting superior with respect to the at least one lumbar access fitting for providing access to skin adjacent the subject's shoulder muscles, and at least one upper arm access fitting on each sleeve, configured to provide sensor access to skin adjacent the subject's upper arm muscles, at least one access fitting on the rib portion of the garment for accessing the subject's rib muscles, at least one triceps access fitting in a triceps portion of the sleeve for access to the subject's triceps muscles, and at least one access fitting on the gluteus maximus portion located inferior with respect to lumbar access fittings, for providing access to skin adjacent the subject's gluteus maximus, and wherein each access fitting is a slit defined for passage of a portion of a sensor device therethrough, the slit being entirely surrounded by a tubing element and being free of any coverings, wherein the tubing element is configured to reinforce the slit, wherein the slit, in an unused state, has at least a portion of opposing edges thereof abutting one-another, and wherein the slit is configured to accommodate a portion of the sensor unit passing therethrough without being overly revealing.

2. A shirt as recited in claim 1, wherein the access fittings on the torso portion consist of two abdominal access fittings configured to provide sensor access to skin adjacent the subject's abdominal muscles, two chest access fittings superior with respect to the two abdominal access fittings configured to provide sensor access to skin adjacent the subject's chest muscles, two lumbar access fittings opposite the two abdominal access fittings configured to provide access to skin adjacent the subject's lumbar muscles, two access fittings on the gluteus maximus portion located inferior with respect to lumbar access fittings, for providing access to skin adjacent the subject's gluteus maximus, two access fittings on the rib portion of the garment for accessing the subject's rib muscles, and one shoulder access fitting superior with respect to the two lumbar access fittings for providing access to skin adjacent the subject's shoulder muscles.

3. A shirt as recited in claim 1, wherein the upper arm access fittings on the pair of sleeves above an elbow of the subject consist of two upper arm access fittings on each sleeve, wherein one of the upper arm access fittings on each sleeve is in a triceps portion of the sleeve for access to the subject's triceps muscles and one of the upper arm access fittings on each sleeve is in a biceps portion of the sleeve for access to the subject's biceps muscles.

4. A shirt as recited in claim 1, wherein each sleeve includes at least one lower arm access fitting inferior with respect to the upper arm access fitting thereof for providing sensor access to skin adjacent the subject's lower arm muscles.

5. A shirt as recited in claim 4, wherein the lower arm access fittings on the pair of sleeves below an elbow of the subject consist of two lower arm access fittings on each sleeve, wherein one of the lower arm access fittings on each sleeve is on a top portion of the lower arm and one of the lower arm access fittings on each sleeve is on a bottom portion of the lower arm opposing the top portion.

6. A shirt as recited in claim 1, further comprising an additional access fitting with a patch of electrically conductive material configured to allow sensor access to the subject's skin by way of electrical signals conducted from the subject's skin, through the patch, to the sensor with the sensor located completely outside the interior space of the torso portion of the garment.

7. A lower garment for wearing during monitoring of muscle activity of a subject, the lower garment comprising:
 a) a torso portion defining an interior space configured and adapted to accommodate and cover at least a portion of the subject's lower torso, and defining an exterior space external to the interior space, wherein a waist opening is defined in the torso portion from the exterior space to the interior space for accommodating the garment being put on and taken off of the subject's lower torso;
 b) a pair of legs attached to the torso portion defining legs of the interior space for accommodating the subjects legs; and
 c) a plurality of access fittings defined in at least one of the torso portion and the pair of legs, each access fitting being configured and adapted to accommodate access to skin of the subject adjacent a muscle group to be monitored by a sensor unit external to the torso portion, such that at least a portion of the sensor unit remains external to the torso portion with the sensor unit accessing the skin via the access fitting, wherein the plurality of access fittings includes at least one access fitting adjacent a hamstring portion of each leg of the garment, at least one access fitting adjacent a quadriceps portion of the leg, opposite the hamstring portion, configured to provide access to skin adjacent to the subject's quadriceps, at least one gluteus maximus access fitting proximate a gluteus maximus portion located superior to the access fitting in the hamstring portion, configured to provide sensor access to skin adjacent the subject's gluteus maximus and gluteus medius muscles, at least one adductor access fitting proximate an adductor portion, and at least one lateral portion access fitting provided substantially lateral with respect to the quadriceps portion and adductor fittings, to provide access to of the subject's upper and lower thighs, and wherein each access fitting is a slit defined for passage of a portion of a sensor device therethrough, the slit being entirely surrounded by a tubing element and being free of any coverings, wherein the tubing element is configured to reinforce the slit, wherein the slit, in an unused state, has at least a portion of opposing edges thereof abutting one-another, and wherein the slit is configured to accommodate a portion of the sensor unit passing therethrough without being overly revealing.

8. A lower garment as recited in claim 7, wherein the access fittings defined in the torso portion of the lower garment consist of two gluteus maximus access fittings proximate a gluteus maximus portion located superior to the access fitting in the hamstring portion, configured to provide sensor access to skin adjacent the subject's gluteus maximus and gluteus medius muscles.

9. A lower garment as recited in claim 7, wherein the access fittings defined in the pair of legs above a knee of the subject consist of one hamstring access fitting on each leg adjacent a hamstring portion of each leg of the garment, configured to provide access to skin adjacent to the subject's hamstrings, one quadriceps access fitting on each leg adjacent a quadriceps portion of the leg, opposite the hamstring portion, configured to provide access to skin adjacent to the subject's quadriceps, one adductor access fitting on each leg proximate an adductor portion, configured to provide access to skin adjacent to the subject's adductors, one access fitting on each leg substantially lateral with respect to a respective quadriceps portion configured to provide access to of the subject's lower thighs, and one access fitting on each leg substantially lateral to a respective adductor fitting configured to provide access to of the subject's upper thighs.

10. A lower garment as recited in claim 7, wherein each leg includes at least one access fitting configured to provide sensor access to skin adjacent the subject's lower leg muscles.

11. A lower garment as recited in claim 7, wherein the access fittings defined in the pair of legs below a knee of the subject consist of one calf access fitting on each leg, configured to provide access to skin adjacent to the subject's calf muscles, and one shin access fitting on each leg, opposite the respective calf access fitting, configured to provide access to skin adjacent to the subject's shin muscles.

12. A lower garment as recited in claim 7, further comprising an additional access fitting with a patch of electrically conductive material configured to allow sensor access to the subject's skin by way of electrical signals conducted from the subject's skin, through the patch, to the sensor with the sensor located completely outside the interior space of the torso portion of the garment.

* * * * *